US009710668B2

(12) United States Patent
Pace et al.

(10) Patent No.: US 9,710,668 B2
(45) Date of Patent: *Jul. 18, 2017

(54) USER TARGETED MEDICAL IMAGING AND INFORMATION PACKAGING, COMPRESSION AND DISTRIBUTION SYSTEM

(71) Applicant: CORISTA, LLC, Concord, MA (US)

(72) Inventors: Charles P. Pace, Manchester Center, VT (US); Eric W. Wirch, Concord, MA (US)

(73) Assignee: Corista LLC, Concord, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/824,315

(22) Filed: Aug. 12, 2015

(65) Prior Publication Data

US 2015/0347460 A1  Dec. 3, 2015

Related U.S. Application Data

(63) Continuation of application No. 13/856,226, filed on Apr. 3, 2013, now Pat. No. 9,110,924, which is a (Continued)

(51) Int. Cl.
*G06F 15/16* (2006.01)
*G06F 21/62* (2013.01)
(Continued)

(52) U.S. Cl.
CPC ...... *G06F 21/6245* (2013.01); *G06F 17/2235* (2013.01); *G06F 17/301* (2013.01);
(Continued)

(58) Field of Classification Search
CPC ... H04L 67/10; G06F 19/3425; G06F 17/3024
(Continued)

(56) References Cited

U.S. PATENT DOCUMENTS 6,348,793 B1  2/2002  Balloni et al.
6,661,228 B2  12/2003  Haworth et al.
(Continued)

FOREIGN PATENT DOCUMENTS

EP        1455305 A2       9/2004
GB   EP 1455305 A2  *  9/2004   ......... G06F 19/3418
(Continued)

OTHER PUBLICATIONS

"Digital Pathology," Sunquest Information Systems, Inc., http://www.sunquestinfo.com/Products/Pages/DigitalPathology.aspx (accessed Mar. 29, 2012).
(Continued)

*Primary Examiner* — Tauqir Hussain
(74) *Attorney, Agent, or Firm* — Wuersch & Gering LLP

(57) ABSTRACT

A computer-based method and system of distributing biological sample data acquired as a digital image of a subject biological sample. The acquired digital image and image capture data are processed according to at least one user. This results in processed image data and capture metadata. The processed image data represents biological sample data of the subject biological sample. A package processing combines the processed image data and capture metadata into a working Package. The method and system enables simultaneous electronic access to the working Package by multiple users, across multiple sectors, in addition to the one user.

18 Claims, 15 Drawing Sheets

Related U.S. Application Data continuation of application No. 12/942,911, filed on Nov. 9, 2010, now Pat. No. 8,504,726, which is a continuation-in-part of application No. 12/843,138, filed on Jul. 26, 2010, now Pat. No. 8,244,912.

(60) Provisional application No. 61/228,819, filed on Jul. 27, 2009.

(51) Int. Cl.

| | | |
|---|---|---|
| *G06K 9/00* | (2006.01) | |
| *G06F 17/30* | (2006.01) | |
| *G06T 7/00* | (2017.01) | |
| *G06F 19/00* | (2011.01) | |
| *H04L 29/08* | (2006.01) | |
| *G06F 17/22* | (2006.01) | |
| *H04L 29/06* | (2006.01) | |

(52) U.S. Cl.
CPC .... *G06F 17/3028* (2013.01); *G06F 17/30247* (2013.01); *G06F 17/30722* (2013.01); *G06F 19/321* (2013.01); *G06F 19/322* (2013.01); *G06F 19/345* (2013.01); *G06F 19/3418* (2013.01); *G06F 19/3425* (2013.01); *G06K 9/00* (2013.01); *G06T 7/0012* (2013.01); *H04L 63/108* (2013.01); *H04L 67/10* (2013.01); *G06T 2200/24* (2013.01); *G06T 2207/10056* (2013.01); *G06T 2207/30004* (2013.01); *G06T 2207/30072* (2013.01)

(58) Field of Classification Search
USPC .................. 709/204, 246, 247, 249; 382/128
See application file for complete search history.

(56) References Cited

U.S. PATENT DOCUMENTS

| | | | |
|---|---|---|---|
| 6,823,203 B2 | 11/2004 | Jordan | |
| 6,859,513 B2 | 2/2005 | Sako | |
| 6,938,156 B2* | 8/2005 | Wheeler ................. | G06F 21/32 380/282 |
| 6,954,767 B1 | 10/2005 | Kanada | |
| 7,028,182 B1 | 4/2006 | Killcommons | |
| 7,302,164 B2 | 11/2007 | Wright et al. | |
| 7,826,649 B2 | 11/2010 | Crandall et al. | |
| 7,944,478 B2 | 5/2011 | Shiibashi et al. | |
| 8,108,228 B2 | 1/2012 | Maresh et al. | |
| 8,116,547 B2 | 2/2012 | Olson et al. | |
| 8,244,912 B2 | 8/2012 | Pace et al. | |
| 8,504,726 B2 | 8/2013 | Pace et al. | |
| 2001/0041991 A1 | 11/2001 | Segal et al. | |
| 2006/0204066 A1 | 9/2006 | Forster et al. | |
| 2006/0274923 A1 | 12/2006 | Forster et al. | |
| 2008/0181472 A1* | 7/2008 | Doi ......................... | G06T 7/00 382/128 |
| 2010/0048159 A1* | 2/2010 | Stenquist ............ | G08B 25/016 455/404.1 |
| 2010/0145990 A1 | 6/2010 | Marcus | |
| 2011/0010192 A1* | 1/2011 | Backhaus ............ | G06F 19/321 705/2 |
| 2011/0022658 A1 | 1/2011 | Pace et al. | |
| 2011/0060766 A1 | 3/2011 | Ehlke et al. | |
| 2011/0158510 A1 | 6/2011 | Aguilar et al. | |
| 2012/0014576 A1* | 1/2012 | Olson ................... | G06F 19/321 382/128 |
| 2012/0069049 A1 | 3/2012 | Howe et al. | |

FOREIGN PATENT DOCUMENTS

| | | |
|---|---|---|
| JP | 2000-276545 A | 10/2000 |
| JP | 2000295462 A | 10/2000 |
| JP | 2006130221 A | 5/2006 |
| JP | 2009-037250 A | 2/2009 |
| JP | 2009-230304 A | 10/2009 |
| KR | 20020004108 A | 1/2002 |
| KR | 1020040082047 A | 9/2004 |
| KR | 1020090006295 A | 1/2009 |

OTHER PUBLICATIONS

"Digital Slide Hosting Service," Aperio Technologies, Inc., http://www.aperio.com/pathology-services/digital-service-slide-hosting.asp>(accessed Mar. 29, 2012).

"Total Digital Pathology," Leica Microsystems http://www.leica-microsystems.com/products/digital-pathology/manage (accessed Mar. 29, 2012).

Lehmann, Thomas M. et al., "Automatic Categorization of medical images for content based retrieval and data mining", Elsevier, Computerized Medical Imaging and Graphics (2005); www.elsevier.com/locate/compmedimag.

Draft Translation of Japanese Office Action for counterpart Japanese application, Dated Mar. 1, 2016.

* cited by examiner

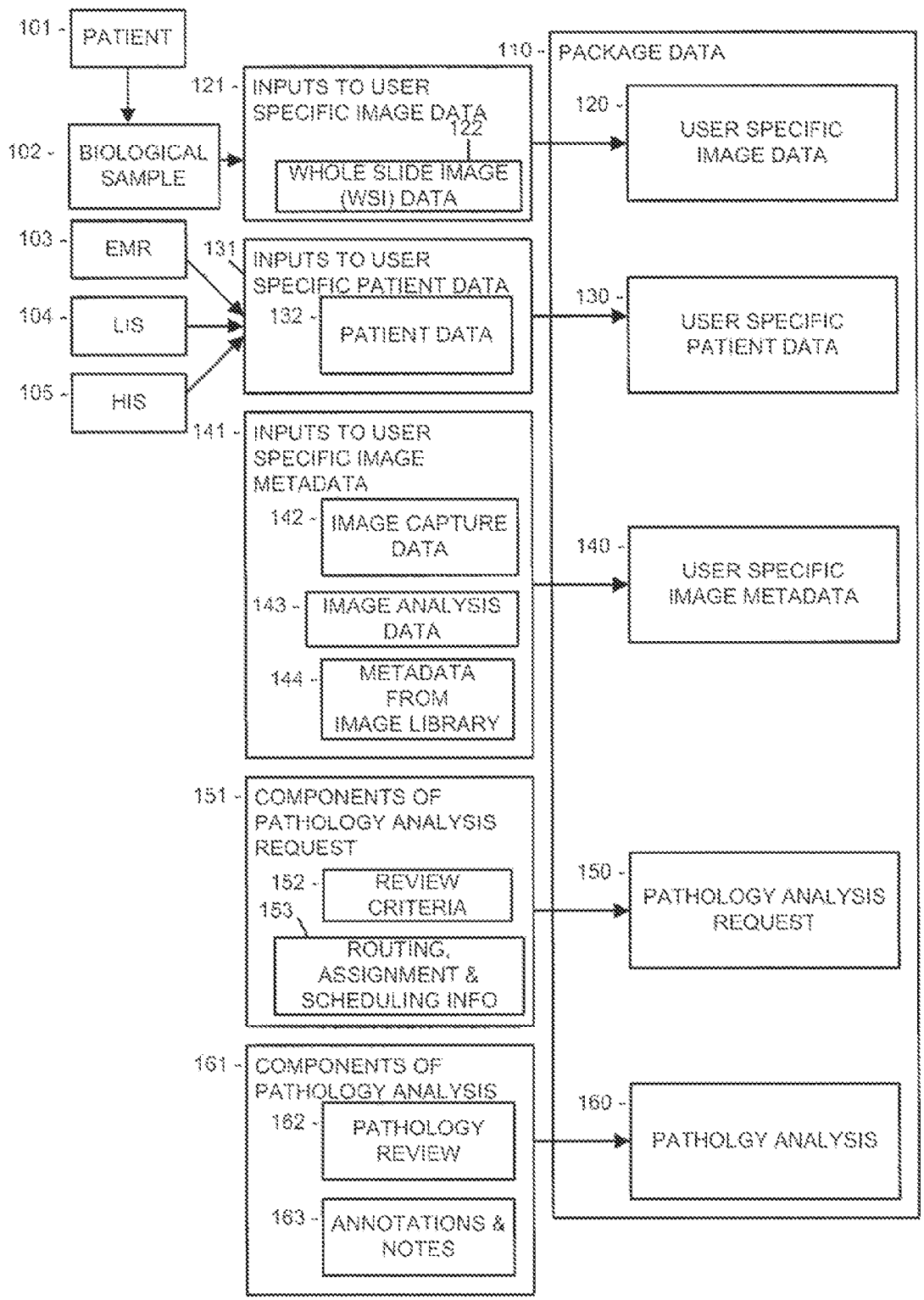
FIG. 1 – PACKAGE & DATA ELEMENTS

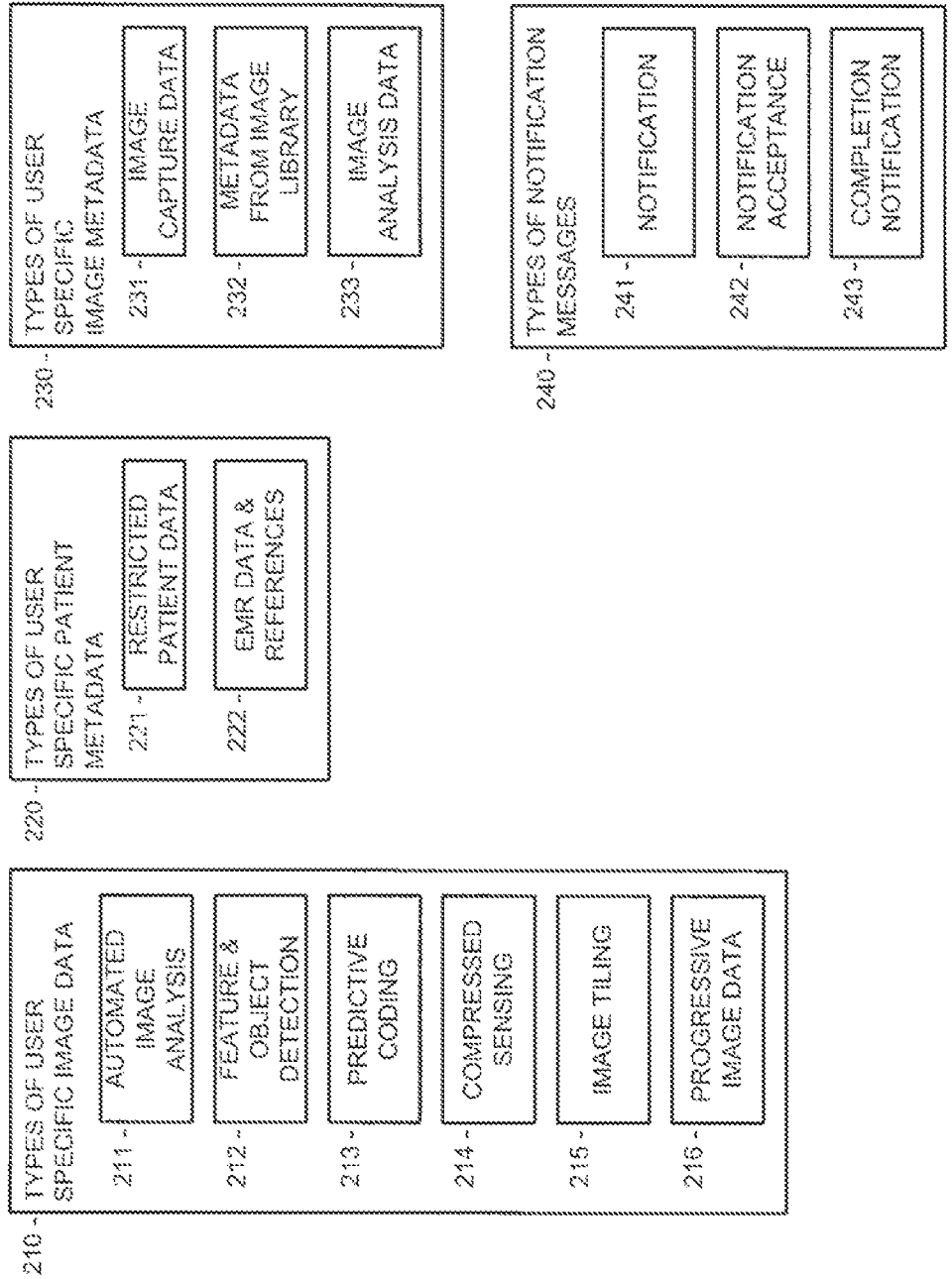

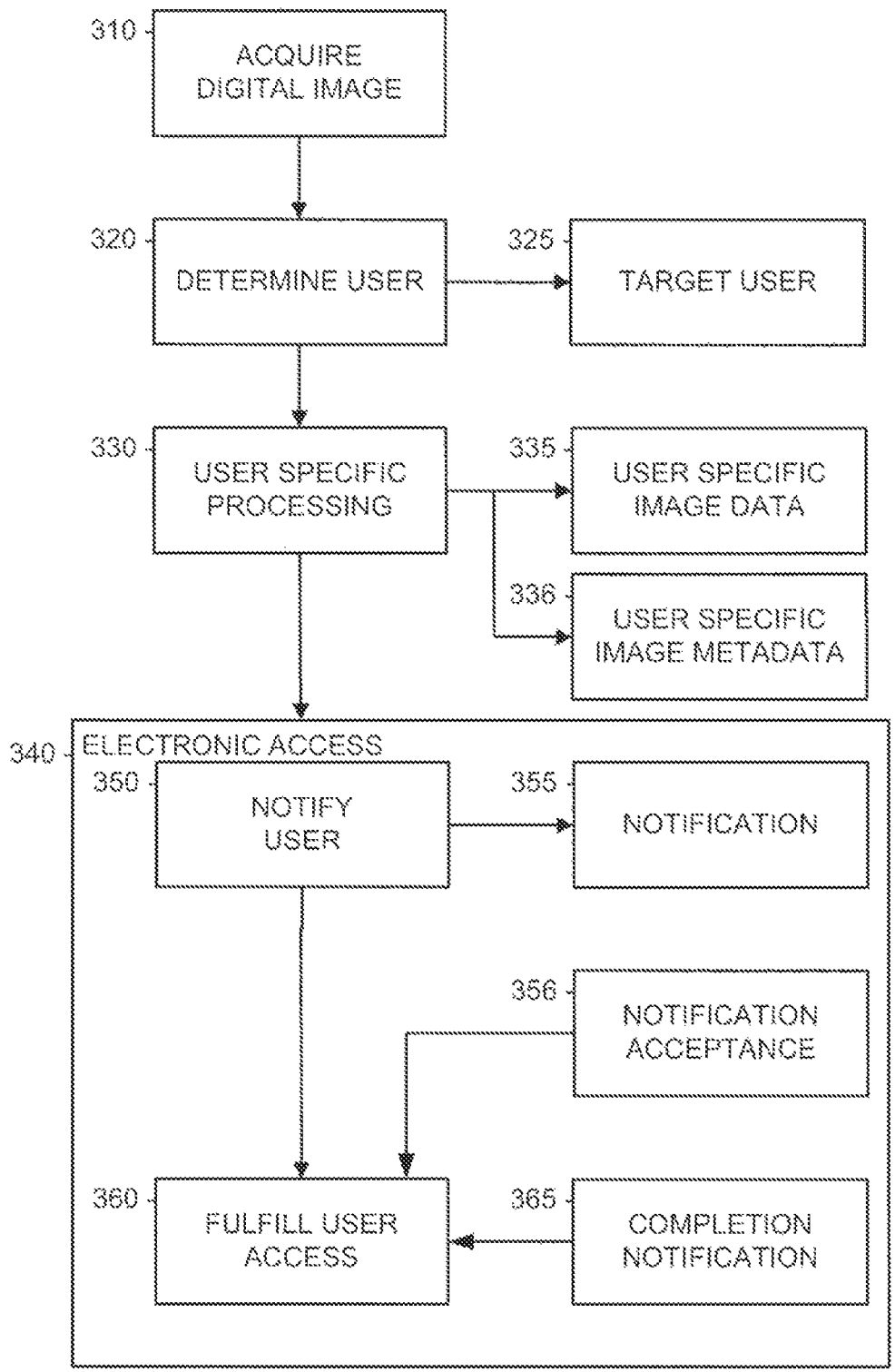

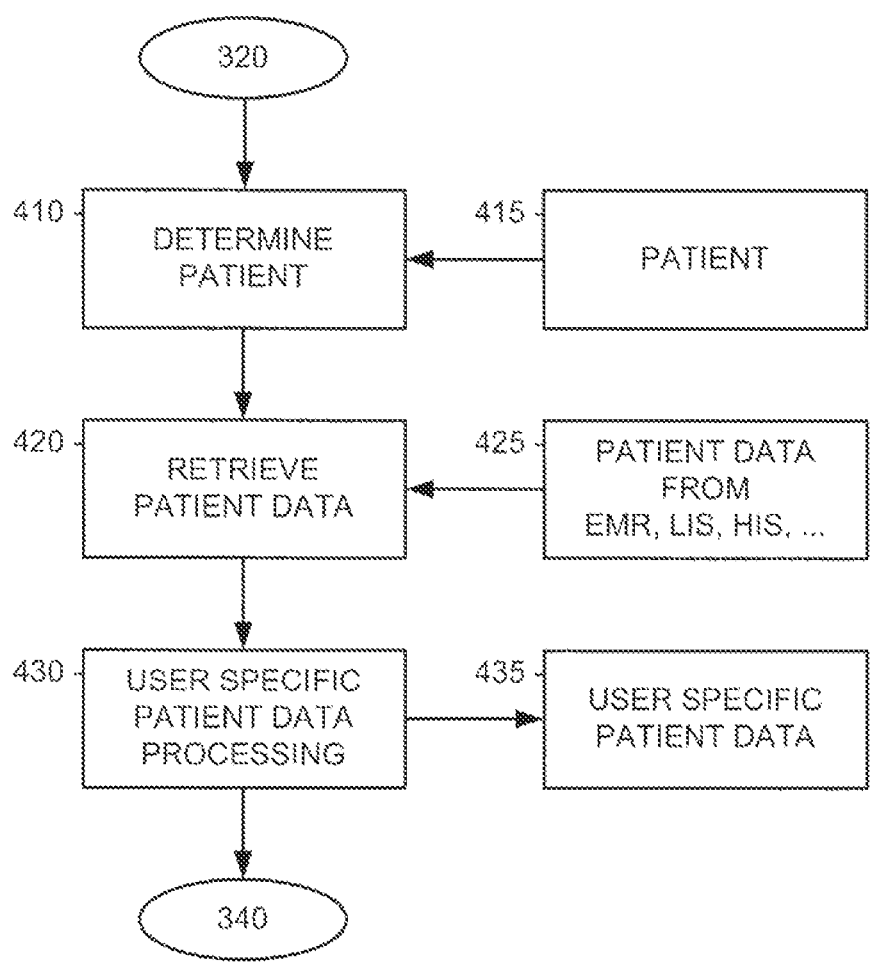
FIG. 4 - COMBINING PATIENT DATA

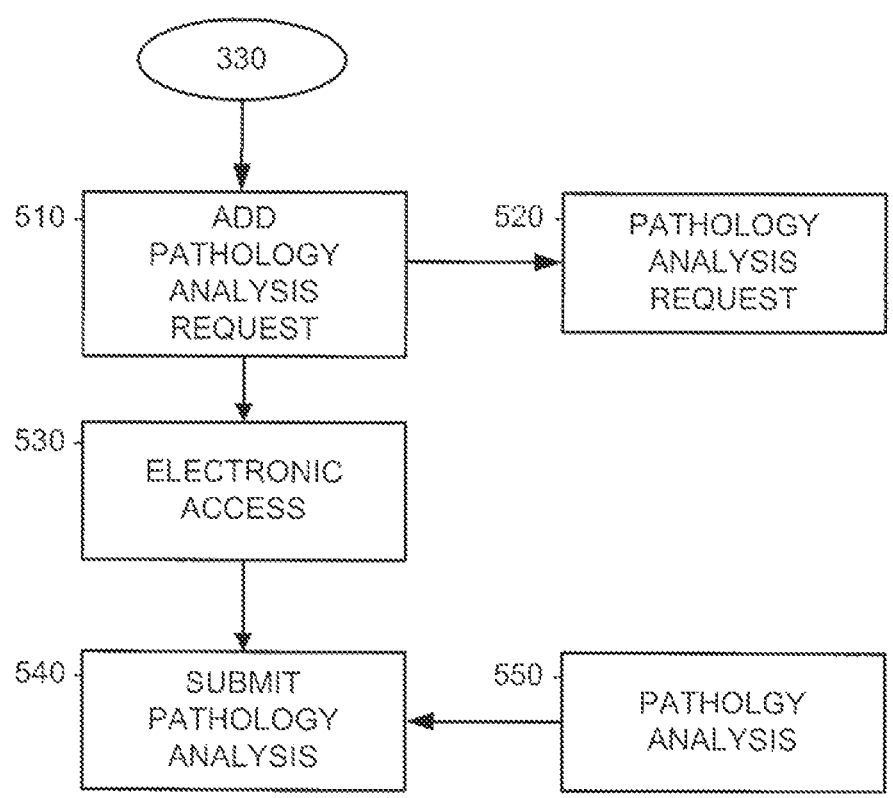
FIG. 5 - PATHOLOGICAL ANALYSIS PROCESS

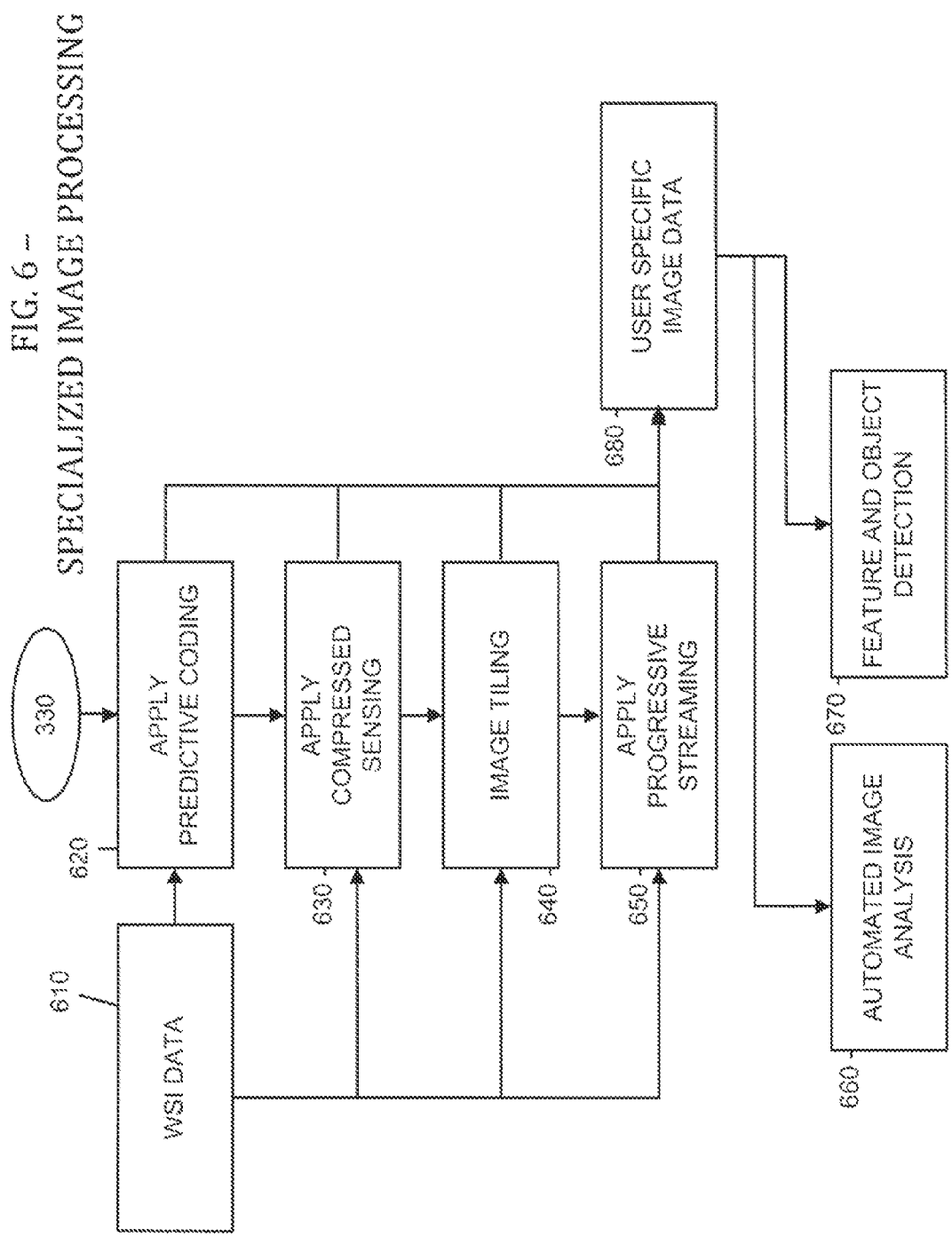

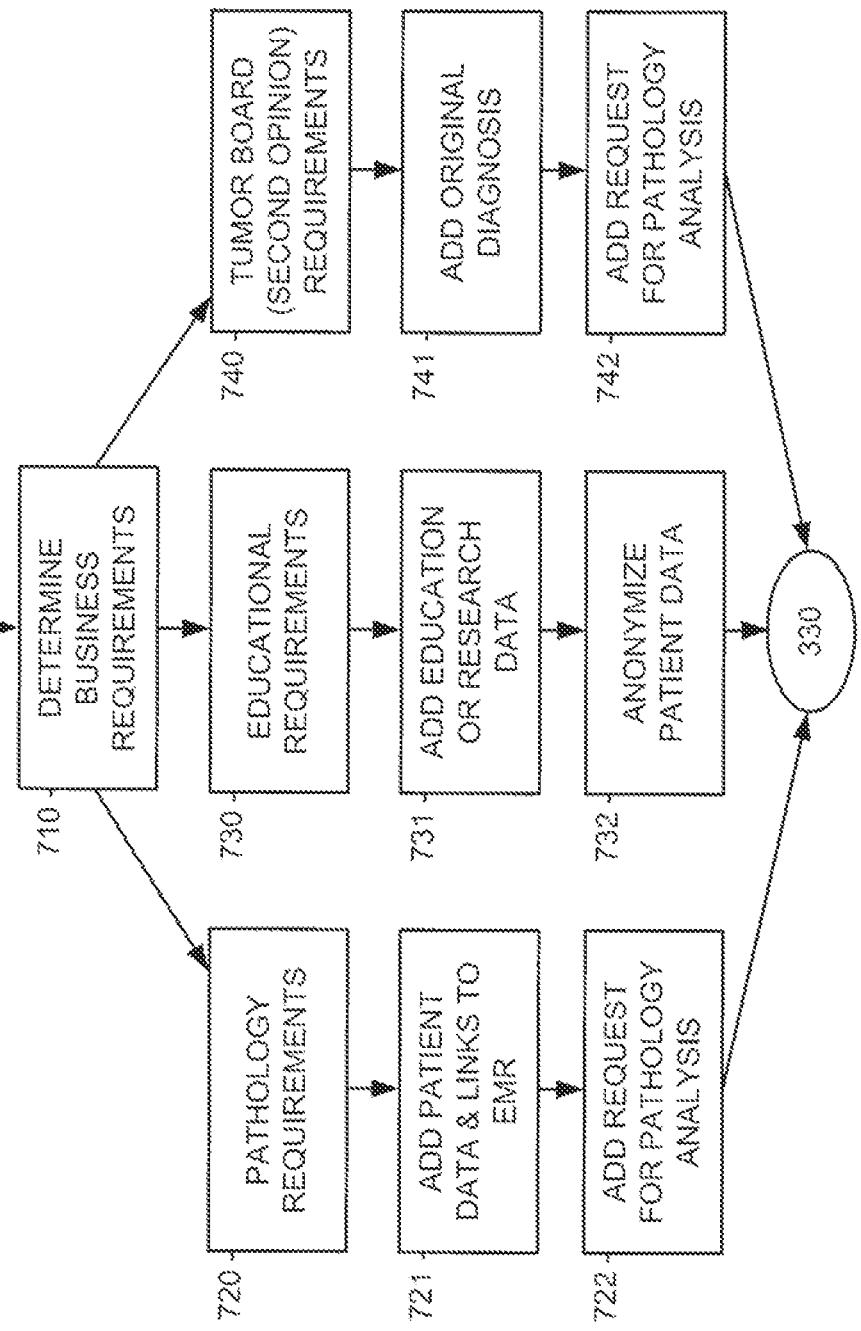

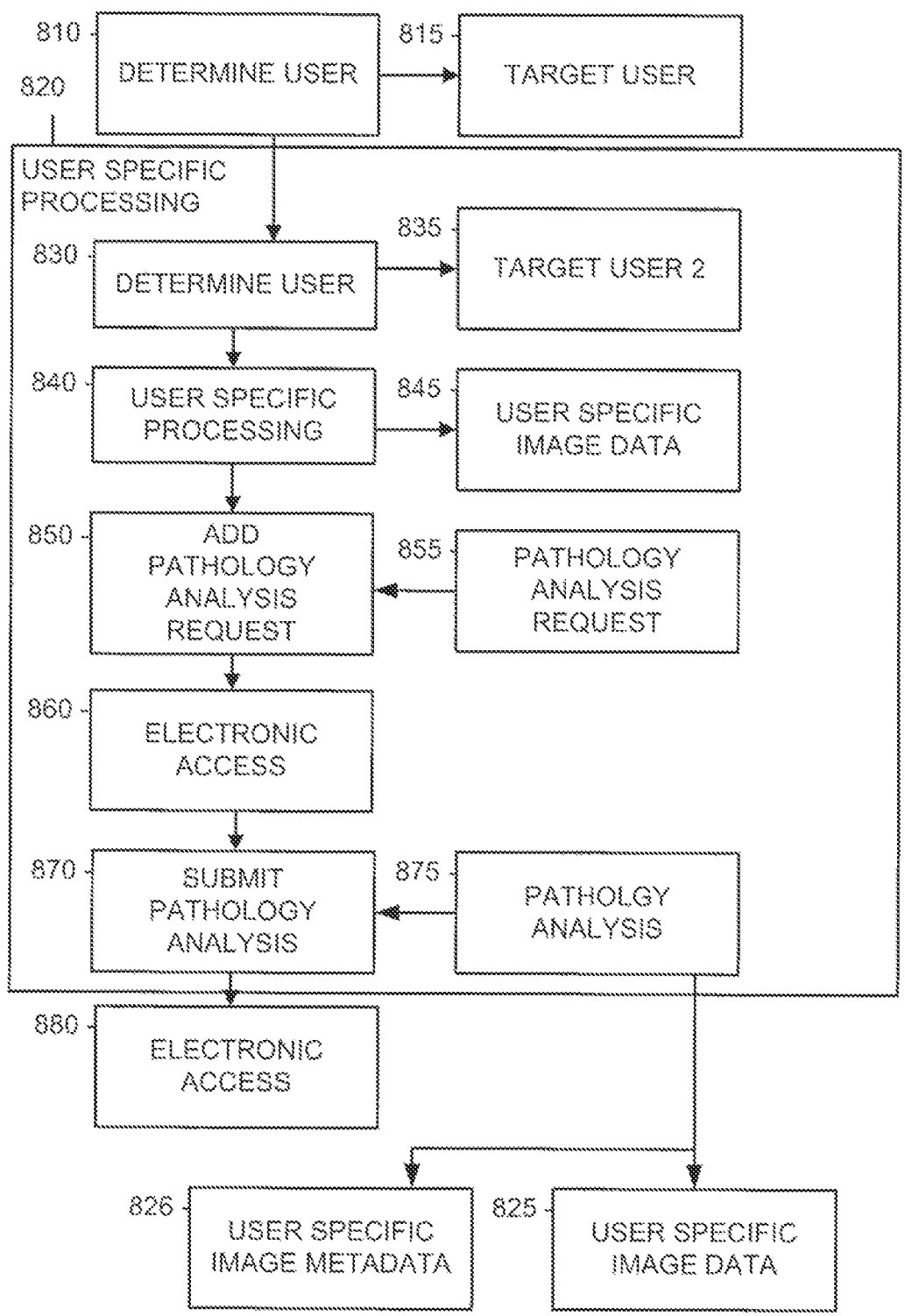
FIG. 8 – RECURSIVE REQUEST FOR DIAGNOSIS

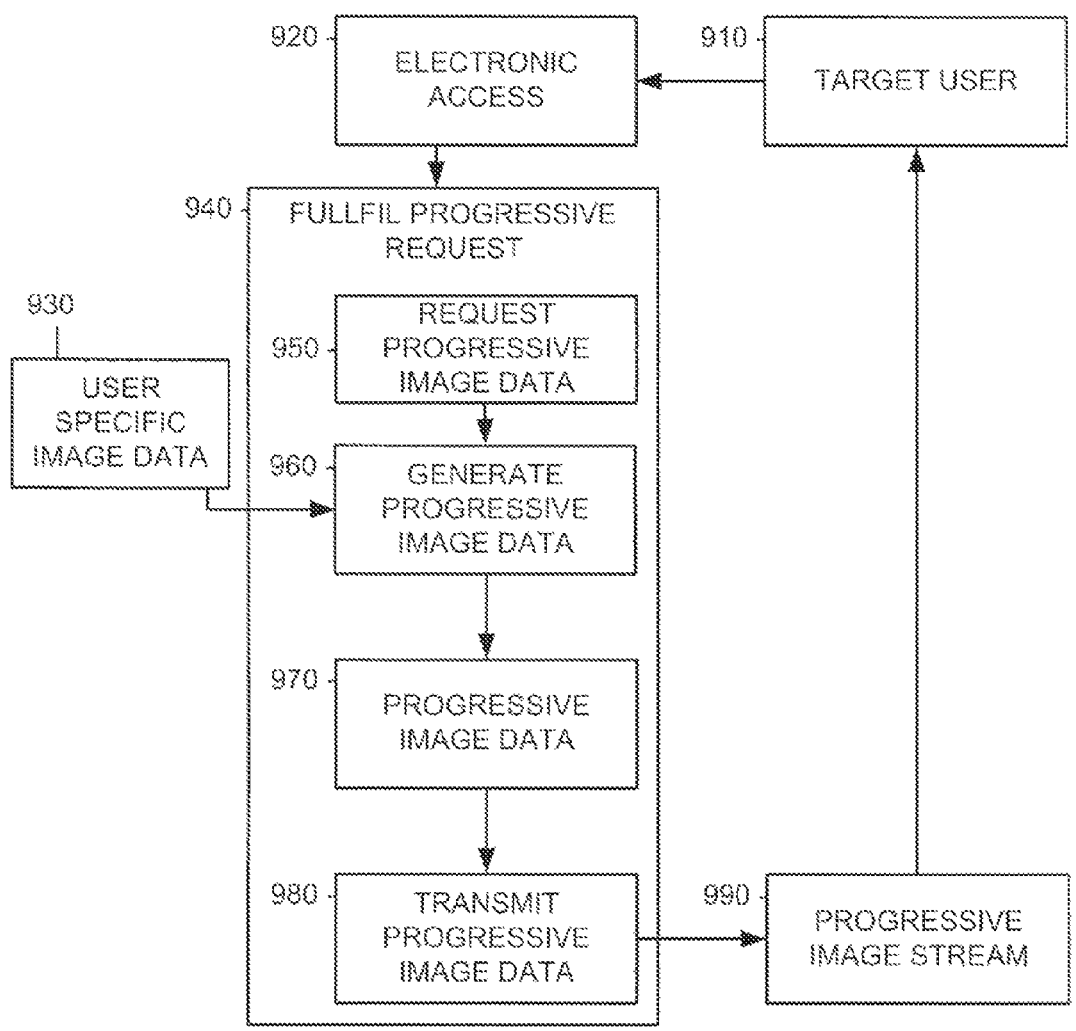

FIG. 10 – GENERATION OF SESSION SAMPLING DATA
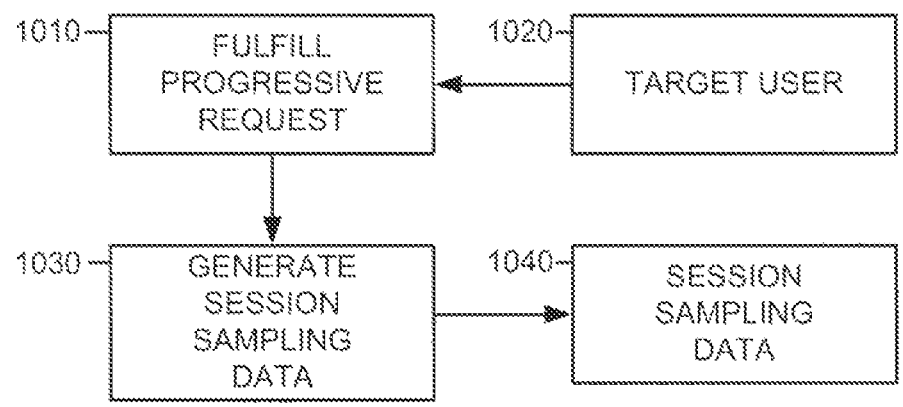

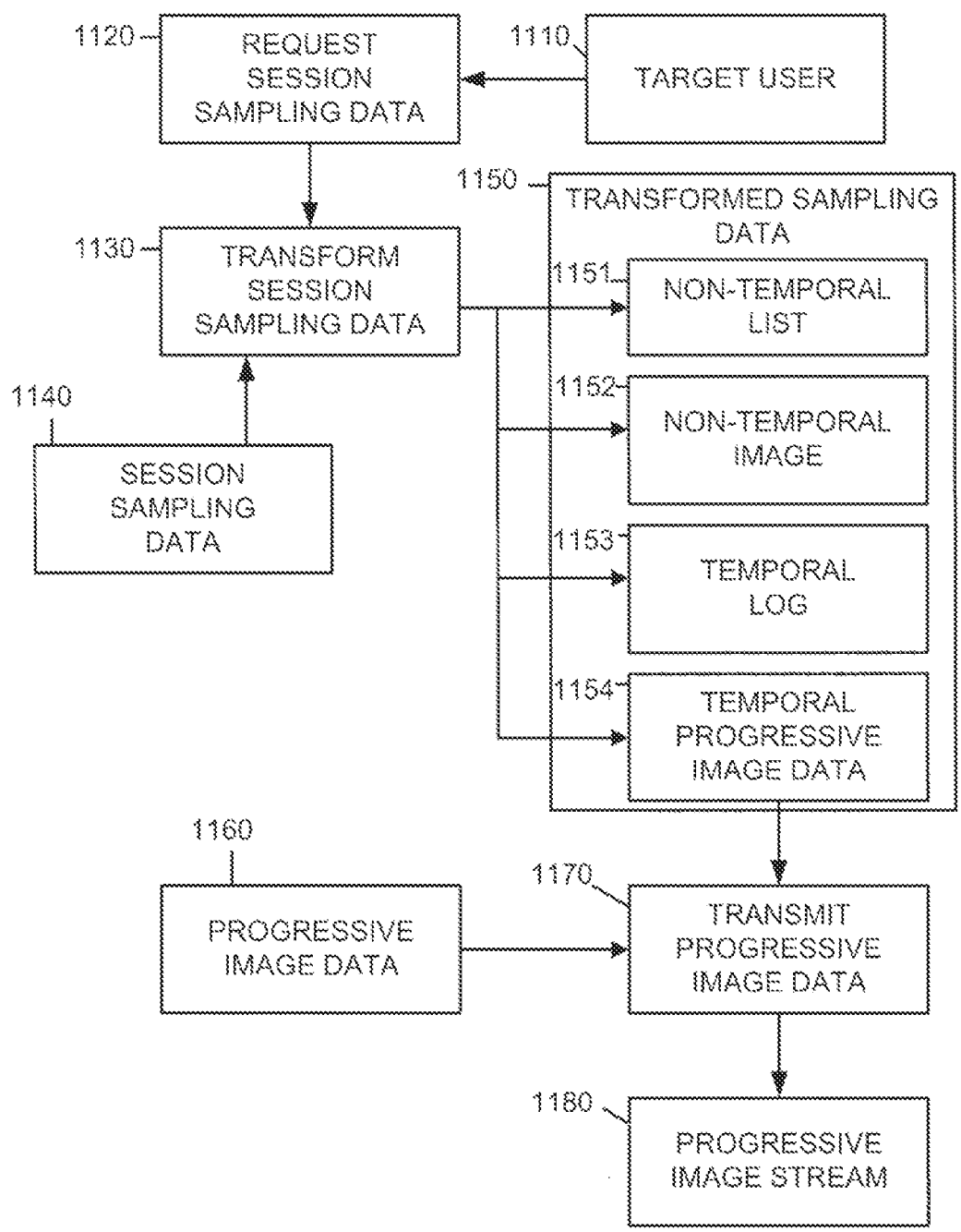

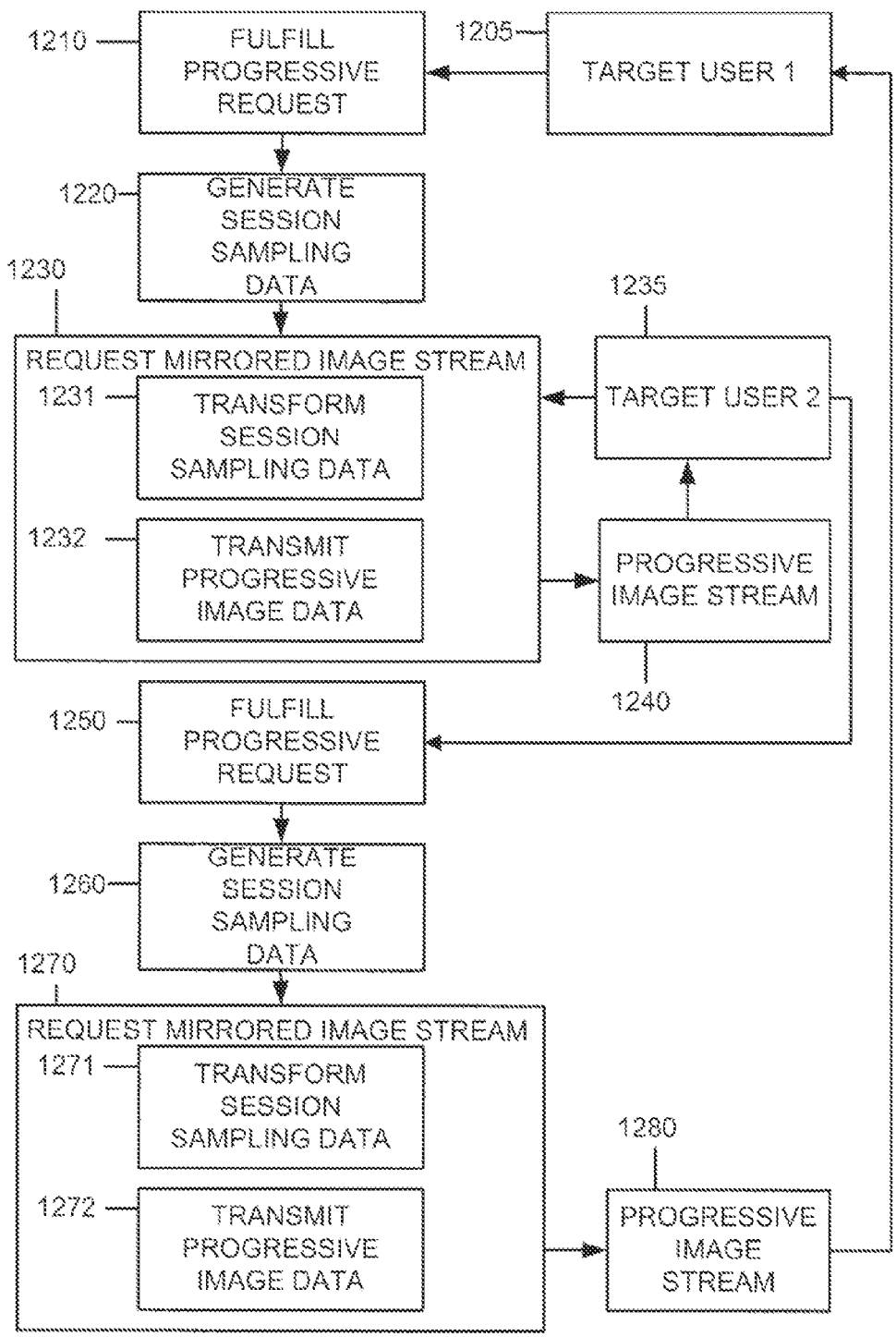

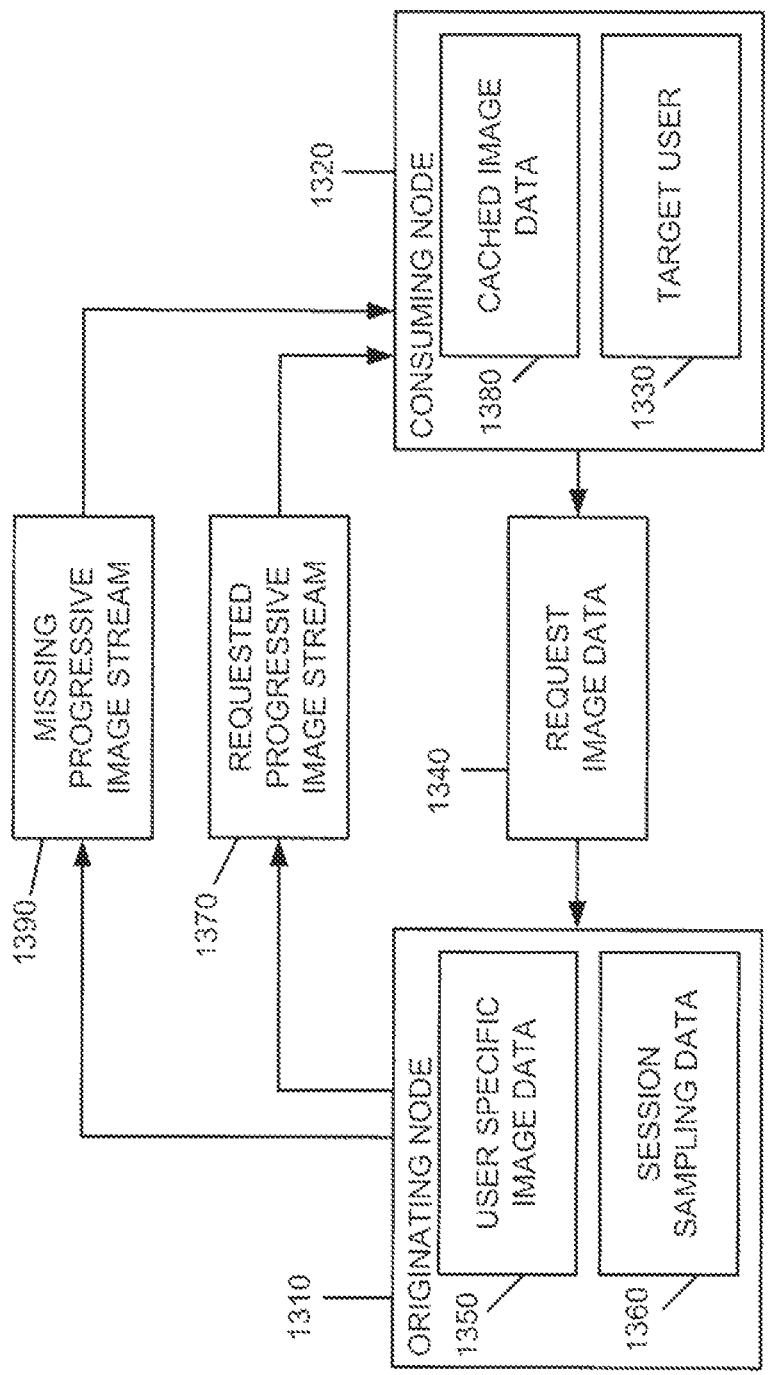
FIG. 13 – CACHING OF ALL PROGRESSIVE IMAGE DATA

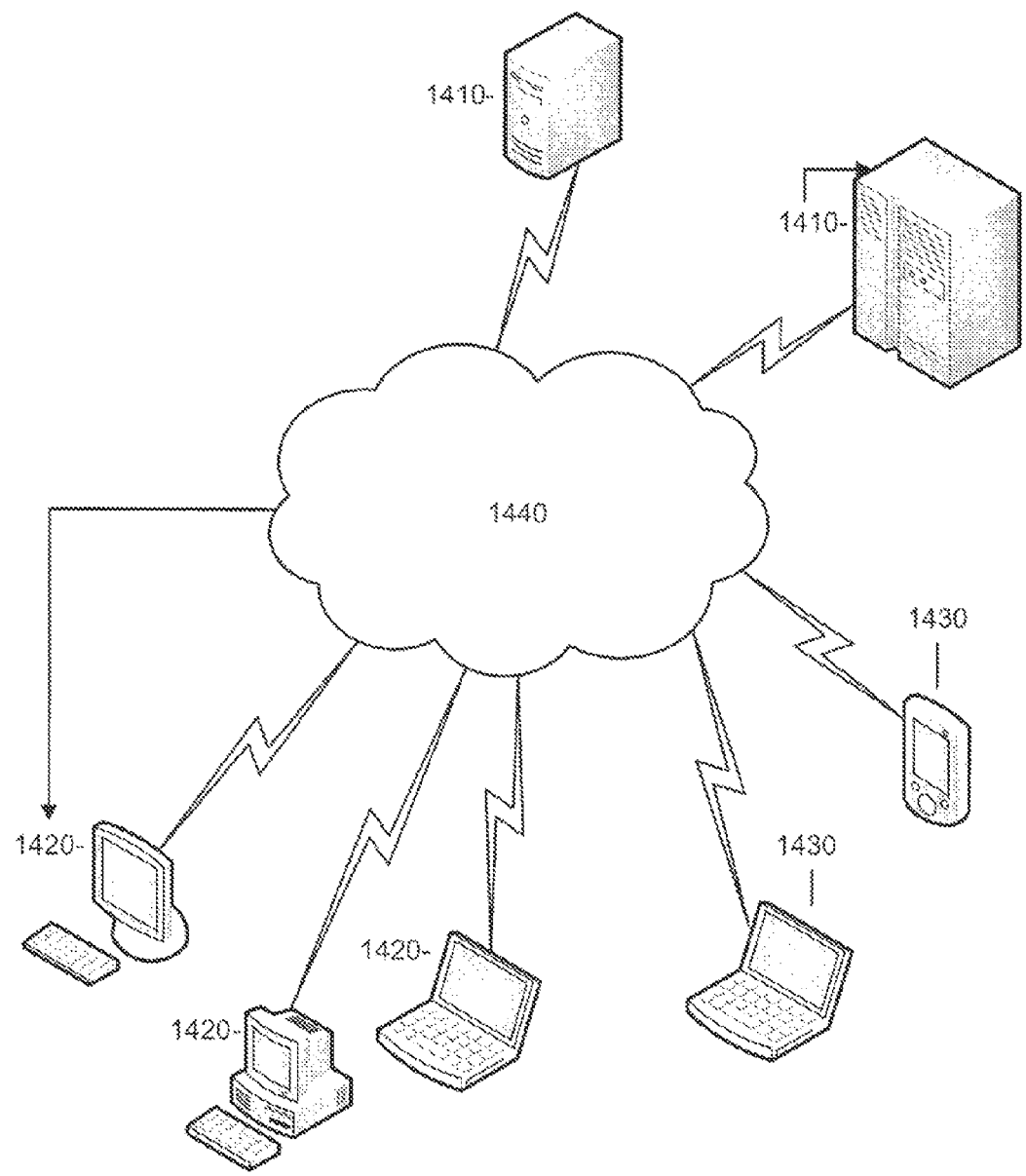
FIG. 14 –
COMPUTER NETWORK ENVIRONMENT SCHEMATIC

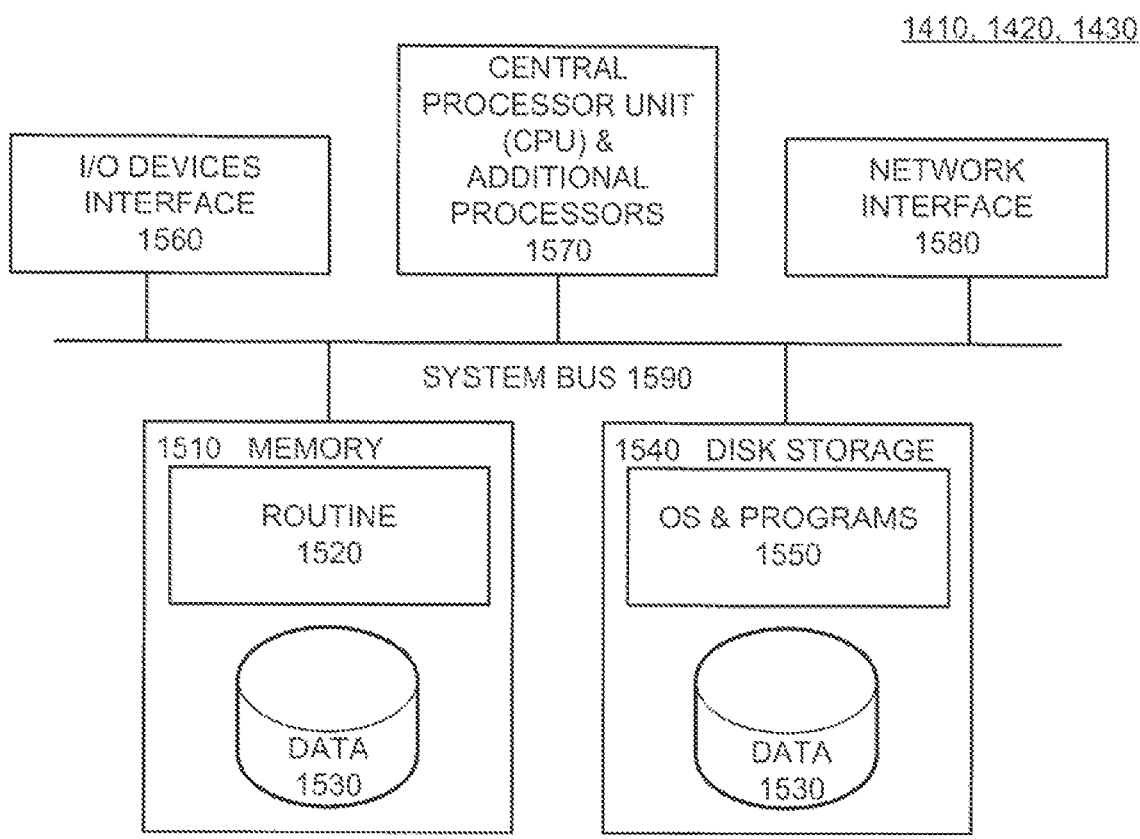

USER TARGETED MEDICAL IMAGING AND INFORMATION PACKAGING, COMPRESSION AND DISTRIBUTION SYSTEM

RELATED APPLICATIONS

This application is a continuation of U.S. application Ser. No. 12/942,911, filed on Nov. 9, 2010, which is a continuation-in-part of U.S. application Ser. No. 12/843,138, filed Jul. 26, 2010, now U.S. Pat. No. 8,244,912, which claims the benefit of U.S. Provisional Application No. 61/228,819, filed on Jul. 27, 2009. The entire teachings of the above application(s) are incorporated herein by reference.

FIELD OF INVENTION

The present invention is in the field of Health Informatics as applied to Pathology, more specifically covering those aspects of Digital Pathology concerned with the imaging, data processing, and data distribution required by and unique to Digital Pathology.

BACKGROUND

In the field of Digital Pathology, there is a requirement to have an exchange of studies for the purpose of a primary or secondary pathological diagnosis. Studies typically consist of one or more lower-resolution images, the references to the corresponding higher-resolution images, associated image metadata, study metadata and patient metadata. Further, access is provided to the necessary data to perform the proper review of the study. Physical and security-based constraints to this access represent a primary barrier to wide scale deployment of Digital Pathology systems. The physical constraints include bandwidth and storage issues for local and remote access, and are typical of most networked applications with the additional requirements imposed by the exceedingly high resolution nature of the data. Additionally, given the sensitivity of medical data, security based constraints, such as ensuring patient privacy and data security are the key areas needing additional focus in this field.

Digital Pathology, in itself, is a compelling enough technology to reach widespread adoption in all but the smallest of practices. The reduction in cost, time and management headache of no longer needing to distribute glass slides to in-house physicians, to second opinion or referrals, to search for slides for publications and presentations will quickly prove itself invaluable, as the workflow of slide production, digitization and immediate archival comes to be. Further, being able to transform, reduce or restrict the data being sent to a user can increase the diagnostic ability of a user, can increase the number of users who can benefit from the data and provide more efficient access to the data.

Digital Pathology provides the opportunity to apply additional processing and analysis on behalf of the user as part of the process, allowing new modalities of diagnosis for the field of Pathology.

Digital Pathology can, as Health Informatics has, enable the filtering of sensitive patient data from a study, allowing the studies use beyond the scope of the hospital, as an educational or research dataset. Structured and encoded information allows new forms of access and distribution of data through the compression, progressive and predictive packaging of the data. Examples of the predictive packaging include only sending the data which the user requires, a resource and bandwidth optimized manner.

SUMMARY

The invention packages and processes Digital Pathology and patient data to be included in a pathology study in such a way as to facilitate the exchange of studies between users. The utility of the invention comes primarily from the transformation of the data into packages that can be used to route and access the information in a manner that automates existing pathology study workflow while enabling additional workflows uniquely suited to the electronic form of pathology study workflow, namely Digital Pathology.

The pathology studies typically consist of one or more digital pathology images, associated or derived image metadata, and patient metadata (FIG. 1—Package and Data Elements) between digital pathology systems.

The data contained within a study needs to be sufficient for the purposes of a targeted user, that user typically being a pathologist. Depending upon what is requested of the pathologist for the pathology review, this may include one or more images of varying, progressively detailed quality, patient data, imaging metadata or the results of preliminary (often automated) analysis, such as measurements, cell counts or other derivative data. Through user specific processing and packaging, the superset of available data is filtered and progressively provided to the target user based on patient privacy, authorization, access restrictions, or simple physical limitations of the target user's connection to the data. This user specific processing and packaging enables simultaneous access of the case by multiple users, each with potentially different imaging and data requirements, each with potentially different permissions on the data, and allows for the auditing of a particular user's session, either collaboratively in real-time or after the fact as an audit trail, teaching tool or other uses.

In one embodiment, a computer-based method of distributing biological sample data includes the steps of:
    acquiring a digital image of a subject biological sample;
    processing the acquired digital image and image capture data according to at least one user, resulting in processed image data and capture metadata, the processed image data representing biological sample data of the subject biological sample;
    through a package processing, combining the processed image data and capture metadata into a Package; and
    enabling simultaneous electronic access to the Package by multiple users, across multiple sectors, in addition to the one user.

Another computer-based method embodying the present invention includes the steps of:
    acquiring a digital image of a subject biological sample;
    processing the acquired digital image to form a progressive image stream representing biological sample data of the subject biological sample, the processing additionally including preparation of access to the progressive image stream, and access being in terms of resolution, scale and sub-regions of the biological sample; and
    transmitting the progressive image stream to one or more users, such that a user views spatially progressive images, in terms of resolution, scale and sub-regions, of the subject biological sample.

According to a computer system of the present invention distributing biological sample data, there is a source of one or more digital (e.g. acquired) images of a subject biological sample. A processor processes a digital image from the source. This processing includes processing the digital image and corresponding image capture data according to at least one user, resulting in (i) processed image data representing biological sample data of the subject biological sample, and (ii) capture metadata. A package process executable by a computer is responsive to the processor processing and is configured to combine the processed image data and capture metadata. This combining forms a package that is electronically accessible simultaneously by multiple users, across multiple sectors, in addition to the one user.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 1 is a schematic view of data elements.

FIG. 2 is a schematic view of details of data elements of the embodiment of FIG. 1.

FIG. 3 is a flow diagram of an initial packaging process of embodiments of the present invention.

FIG. 4 is a flow diagram of a process combining patient data with a package in the FIG. 3 embodiment.

FIG. 5 is a flow diagram of a pathological analysis in one embodiment.

FIG. 6 is a schematic flow diagram of image processing in one embodiment.

FIG. 7 is a schematic illustration of sector specific processing in one embodiment.

FIG. 8 is a schematic flow diagram of recursive User Specific Processing in the FIG. 5 embodiment.

FIG. 9 is a schematic flow diagram of generation of a progressive image stream in embodiments.

FIG. 10 is a block diagram of the generation of session sample data in embodiments.

FIG. 11 is a flow diagram of access and transformation of the session sampling data of FIG. 10.

FIG. 12 is a block diagram of real-time mirrored progressive image session in embodiments.

FIG. 13 is a schematic diagram of caching of progressive image data in an embodiment.

FIGS. 14 and 15 are schematic and block diagrams, respectively, of a computer network and computer nodes in which embodiments are deployed.

DETAILED DESCRIPTION

FIG. 1 is an overview of the package and data elements contained in one embodiment of the present invention (i.e., the invention system). A package (110), which is equivalently referred to as a study, is a user-specific grouping of images and metadata.

The first element of the package is User Specific Image Data (120), which is the result of User Specific Processing (330) on a Whole Slide Image (122), equivalently referred to as a WSI or Whole Slide Image Data or WSI Data. A WSI is obtained by capturing a digital image of a Biological Specimen (102), which is equivalently referred to as a Biological Sample, from a Patient (101).

The second element of the package is User Specific Patient Metadata (130), which is the result of User Specific Processing (330) of Patient Data (132). Patient Data is retrieved from an Electronic Medical Record (103), equivalently referred to as EMR, Laboratory Information System (104), equivalently referred to as LIS, or Hospital Information System (105), equivalently referred to as HIS, or other systems containing patient data.

The third element of the package is User Specific Image Metadata (140), which may be generated from data obtained at the time of Image Acquisition, data from a library of similar images or from automated or preliminary image analysis.

The fourth and fifth elements of the package are a Pathology Analysis Request (150) to the target user (325), which will result in that user generating and adding a Pathology Analysis (160) back into the package (110). Data contributing to the Pathology Analysis Request (150) include Review Criteria (152) and Routing, Assignment and Schedule Information (153). The components of the Pathology Analysis (160) may include some format of a Pathology Review (162) and Annotations and Notes (163).

FIG. 2 details various types of package (110) data and messages.

Types of User Specific Image Data (210, also equivalent to 120 in FIG. 1) may include one of several forms of derived image data, which may include Automated Image Analysis Data (211) or Feature and Object Detection Data (212), or various transformations of the WSI Data including Predictive Coding Data (213), Compressed Sensing Data (214), Image Tiling Data (215), and Progressive Image Streaming Data (216).

Types of User Specific Patient Metadata (220, also equivalent to 130 in FIG. 1) may include Restricted Patient Data (221), EMR Data and References (222).

Types of User Specific Image Metadata (230, also equivalent to 140 in FIG. 1) may include Image Capture Data (233), Metadata from Image Library (234) and Image Analysis Data (143).

Types of Notification Messages (240) may include Notifications (241), Notification Acceptance (242) and Completion Notification (243) messages.

FIG. 3 is an overview of the Initial Packaging Process, where a package is created for a user containing images acquired from a biological specimen.

In the first step, Acquire Digital Images (310), a Whole Slide Digital Image (WSI) (122 in FIG. 1) is captured from the physical biological specimen (102 in FIG. 1) and a new package 110 (FIG. 1) is created. During the Determine User (320) step, one or more target users (325) for the package are determined. Next, any required User Specific Processing (330) for the Target Users is performed on the WSI (122) data to generate User Specific Image Data (335, equivalent to 120 in FIG. 1) and User Specific Image Metadata (336, equivalent to 140 in FIG. 1) which is added to the package for the target users.

Once the package has the necessary elements for the target user, Electronic Access (340) is enabled for the target users. Electronic access is initiated by sending each target user a Notification Message (355, equivalent to 241 in FIG. 2) during the Notify User (350) step. The notification message alerts the target user that the package is complete and ready for user access. The Target User may optionally send a Notification Acceptance Message (356, equivalent to 242 in FIG. 2) signaling acceptance or rejection of the package. If accepted, the package is then accessed by the target users wholly or in part as part of the Fulfilling User Request step (360). When the Target User is done accessing the package, a Completion Notification (365) message is sent to the originator signaling that they done accessing the package.

FIG. 4 depicts the combination of Patient Data with a Package. In addition to User Specific Processing of the WSI Data from the Initial Packaging Process (FIG. 3), it may be determined that the user also requires Patient Data in the package.

Within the scope of User Specific Processing (330 in FIG. 3), the first additional step is to Determine Patient (410), where the patient (415, also at 101 in FIG. 1) associated with the package (110 in FIG. 1) is determined. Next, in the Retrieve Patient Data step (420), Patient Data (425, also 132 in FIG. 1) is requested and retrieved from an external system. Additional User Specific Patient Data Processing (430) may then be performed on the Patient Data 425, 132 to generate User Specific Patient Data (435, also 130 in FIG. 1) to be included in the Package. Finally, normal processing then continues onto the Notify User step (350 in FIG. 3) of the Initial Package Process (FIG. 3).

FIG. 5 depicts adding both a Request for Pathology Analysis and the resulting Pathology Analysis to the Package.

During User Specific Processing (330 in FIG. 3), an additional step Add Pathology Analysis Request (510) includes a Request for Pathology Analysis (520, and 150 in FIG. 1) in the package (110 of FIG. 1). Processing then continues on to the Electronic Access step (530, also 340 in FIG. 3) of the Initial Packaging Process (FIG. 3). During the Fulfill User Request step (360 in FIG. 3), the user adds a Pathology Analysis (550, also 160 in FIG. 1) to the Package (110 in FIG. 1) by the Target User (325 in FIG. 3) during the Submit Pathology Analysis step (540).

FIG. 6 depicts an extension of the User Specific Processing 330 on the WSI Data during the Packaging Process (FIG. 3).

Specialized User Specific Processing 330 (FIG. 3) of the WSI Data 122 (FIG. 1) may include Automated Image Analysis 211 (FIG. 2), Feature and Object Detection 212 (FIG. 2), Predictive Coding 213 (FIG. 2), Compressed Sensing 214 (FIG. 2), Image Tiling 215 (FIG. 2), and Progressive Image Streaming Data 216 (FIG. 2) to package 110.

During the User Specific Processing 330 (FIG. 3) step, in addition to other processing, Predictive Coding (620, equivalent to 213 of FIG. 2) may be applied to the WSI Data (610, equivalent to 122 of FIG. 1), resulting in Predictive Coding Data (213 of FIG. 2). Additionally, Compressed Sensing (630) may be applied to the WSI Data 610, 122, resulting in Compressed Sensing Data (214 of FIG. 2). Additionally, the WSI Data may be staged for Progressive Streaming (640) depending on the user's image requirements, resulting in Progressive Image Streaming Data (at 216 of FIG. 2). Additionally, the WSI Data may be processed for Image Tiling (640), resulting in Image Tiling Data (215 of FIG. 2).

As a result of these processes, Automated Image Analysis data (660, equivalent to 211 of FIG. 2) and Feature and Object Detection data (670, equivalent to 212 of FIG. 2) is generated.

All of the data generated in these steps is added to the package 110 (FIG. 1) as User Specific Image Data (680, equivalent to 120 in FIG. 1). Finally, normal processing (FIG. 3) continues with the Electronic Access step (340).

FIG. 7 depicts Sector Specific Processing (also known as Business Requirement Enhanced User Specific Processing), where the details of user determination and User Specific Processing 320, 330 (FIG. 3) are based not only on user but also by functional/business requirements. This demonstrates how one or more different packages may be assembled based on the same WSI and metadata to produce products for various users.

During the determination of the user's business requirements (710), the package can undergo a plurality of packaging functions, one of which is packaging for a pathology review (FIG. 7, nodes 720, 721, 722, which are equivalent to FIG. 5).

A second example packaging might be for education or research (730). For education and research, education or research data is added (731), such as the scope of a study, or the focus of a particular analysis, and the patient metadata in the package is filtered to remove identifying patient information (732).

Yet another non-limiting packaging might be for review by a tumor board or second opinion (740). This is a specific instance of a Recursive Request for Diagnosis, in which one of the metadata items of the package is a Pathology Analysis 160 (FIG. 1) that has been generated through an independent Pathological Analysis Process (FIG. 5). This recursive process is described in greater detail in FIG. 8. In this embodiment, after a package has gone through a Pathology Analysis Process (FIG. 5), a new package, including the Pathology Analysis (741, equivalent to 160 in FIGS. 1 and 550 in FIG. 5) from the original review (530) is generated, which is intended for review by additional target users. The new target users are then notified (at 350 in FIG. 3), and these users fulfill the request (742 of FIG. 7) submitting their own Pathology Analysis (at 540 in FIG. 5).

FIG. 8 shows how User Specific processing to produce User Specific Image Data may recursively initiate another Request for Pathology Analysis to a second Target User in order to generate the data required to perform the first request.

During the Determine User (810, equivalent to 320 in FIG. 3) step, the Target User (815, equivalent to 325 in FIG. 3) is determined. During the User Specific Processing (820, equivalent to 330 in FIG. 3) step, it is determined that an additional Pathology Analysis is necessary in order to fulfill the data requirements of the original Target User (815). At this point, the Second Target User (835) is determined through a second Determine User (830) step. Following the process in FIGS. 3 and 5, User Specific Processing (840, equivalent to 330 in FIG. 3) for the second target user (835) is performed, resulting in User Specific Image Data (845, equivalent to 335 in FIG. 3). A Pathology Analysis Request (855, equivalent to 520 in FIG. 5) is added to the package in Add Pathology Analysis Request (850, equivalent to 510 in FIG. 5). The Second Target User then is provided Electronic Access (860, equivalent to 530 in FIGS. 5 and 340 in FIG. 3) to the package for the purpose of a Pathology Review. The final step for the Second Target User is adding a Pathology Analysis (875, equivalent to 550 in FIG. 5) to the Package during the Submit Pathology Analysis (870, equivalent to 540 in FIG. 5) step. The Second Target User's Pathology Analysis is then added in whole or part to the original Target User's package, and contributes to that user's User Specific Image Data (825, equivalent to 335 of FIG. 3) and User Specific Image Metadata (826, equivalent to 336 of FIG. 3). Finally, the first user is provided Electronic Access (880, equivalent to 340 of FIG. 3) to their package.

FIG. 9 shows the generation of a stream of Progressive Image Data in response to a user request for Progressive Image Data.

A Target User (910, equivalent to 325 in FIG. 3) has been provided Electronic Access (920, equivalent to 340 in FIG. 3) to a package containing User Specific Image Data (930, equivalent to 335 in FIG. 3). In the Fulfill the Progressive Request Procedure (940), the Target User lodges or otherwise initiates a Request for Progressive Image Data (950). The Generate Progressive Image Data (960) step is triggered by that request, resulting in Progressive Image Data (970, equivalent to 216 in FIG. 2). That data is then transmitted to the requesting target User in the Transmit Progressive Image Data (980) step as a Progressive Image Stream (990) back to the Target User 910, 325.

FIG. 10 shows the generation of Session Sampling Data during the course of the generation of a stream of Progressive Image Data such as at 990 in FIG. 9.

During the Fulfill Progressive Request (1010, equivalent to 940 in FIG. 9) step in response to a Request of Progressive Data by a Target User (1020, equivalent to 910 of FIG. 9), Session Sampling Data (1040) is created during the Generate Session Sampling Data (step 1030), recording the details of the Progressive Image Data request by the Target User.

FIG. 11 shows the Access and Transformation of Session Sampling Data. As a the result of a Target User 910 requesting a Progressive Image Stream 990 of FIG. 9, which in turn generates Session Sampling Data 1040 (FIG. 10), that Session Sampling Data may be accessed and transformed by the original or other target users.

A Target User (1110) generates a Request Session Sampling Data (1120) message, which triggers a process to Transform Session Sampling Data (1130). The Transform Session Sampling Data process (1130) takes the Session Sampling Data (1140, equivalent to 1040 of FIG. 10) and generates Transformed Sampling Data (1150). Transformed Sampling Data (1150) may take the form of: a Non-Temporal List (1151) of requested regions and resolutions; a Non-Temporal Image (1152) of the requested regions and resolutions; a Temporal Log (1153) of requested regions and resolutions, including the absolute or relative request time; or as Temporal Progressive Image Data (1154) of requested regions and resolutions, including the absolute or relative request time.

Further, the Temporal Progressive Image Data (1154) may be combined with the original Progressive Image Data (1160, equivalent to 970 FIG. 9) through a Transmit Progressive Image Data (1170) process to generate a Progressive Image Stream (1180, equivalent to 990 in FIG. 9) which mirrors the relative Progressive Image Stream of the original session used to generate the Session Sampling Data (1040, 1140).

FIG. 12 shows two users who are in a synchronized, Real Time Mirrored Progressive Image Session. This Mirrored Session is achieved through a second Target User consuming Transformed Session Sampling Data (1150) while it is being generated by the first Target User. Also shown is how, at any point in the shared session, either user may take control of the session, generating a new progressive image stream which is mirrored to both users.

A Target User (1205, equivalent to 1020 in FIG. 10) initiates a progressive image data request, which is processed in the Fulfill Progressive Request (1210, equivalent to 1010 of FIG. 10) step, which then Generates Session Sampling Data (1220, equivalent to 1030 of FIG. 10). Target User 2 (1235, equivalent to 1110 in FIG. 11) Requests a Mirrored Image Stream (1230), which is equivalent to the Transformation of Session Sampling Data (1231, equivalent to step 1130 in FIG. 11) and Transmission of Progressive Image Data (1232, equivalent to step 1170 in FIG. 11) from FIG. 11. The resulting Progressive Image Stream (1240, equivalent to 1180 in FIG. 11) is sent to Target User 2.

Through the act of generating an additional progressive image data request by Target User 2, a second Fulfill Progressive Request (1250) step is entered, which in turn Generates Session Sampling Data (1260). Target User 1, who is part of the Mirrored Progressive Image Session implicitly initiates a second Request Mirrored Image Stream (1270) step, Transforming Session Sampling Data (1271) and Transmitting Progressive Image Data (1272) in turn, generating a new respective Progressive Image Stream (1280) to Target User 1, effectively mirroring the actions of Target User 2 to both users.

FIG. 13 shows how a remote user may cache the viewed portions of the User Specific Image Data (120, 210, 335, 680, 825, 930) through the local storage of the requested Progressive Image Data (970, 1160), or may cache the entire User Specific Image (120, 210, 335, 680, 825, 930) through the use of a second Progressive Image Stream containing only the User Specific Image Data which was not originally requested, resulting in User Specific Image residing on the Consuming Node in its entirety, providing a reference copy of the original User Specific Image Data.

User Specific Image Data (1350, equivalent to data 930 in FIG. 9) resides on an Origination Node (1310). A Target User (1330, equivalent to user 910 in FIG. 9) on a Consuming Node (1320) generates a Request for Image Data (1340, equivalent to 950 in FIG. 9). The request is processed as in FIG. 9, and the resulting Requested Progressive Image Stream (1370, equivalent to image stream 990 in FIG. 9) is sent from the Originating Node (1310) to the Consuming Node (1320). On the Originating Node (1310), Session Sampling Data (1360, equivalent to data 1040 in FIG. 10) is generated. On the Consuming Node (1320), the Requested Progressive Image Stream (1370) is both cached as Cached Image Data (1380) and forwarded to the Target User (1330), representing the consumed Progressive Image Stream. Optionally, at the conclusion of the Target User's session, the remainder (of the User Specific Image Data 1350) referred to as Missing Progressive Image Stream (1390) may be sent to the Consuming Node (1320), where it will be added to the Cached Image Data (1380), making the Cached Image Data (1380) a duplicate copy of the original User Specific Image Data (1350).

FIG. 14 is a schematic view of a computer network environment in which embodiments of the invention are deployed. In one embodiment, the network includes one or more servers (1410), one or more desktop or notebook clients (1420) and one or more notebook or other wireless clients (1430) connected via a communications or similar network (1440).

FIG. 15 is a block diagram of a computer node of the network of FIG. 14. Components of the computer node include a System Bus (1590) connecting I/O Device Interfaces (1560), a Central Processor Unit (CPU) and Additional Processors (1570), Network Interfaces (1580), Memory (1510) and Disk Storage (1540). Memory may contain both Routines (1520) and data (1530), and Disk Storage may contain both an Operating System (OS) & Programs (1540) and Data (1530). In particular the Routines 1520, Programs 1550, and data 1530 include the processes and data of FIGS. 1-13 which configure computers/devices 1410, 1420, 1430 to form embodiments of the present invention as made clear below.

A description of example embodiments of the invention follows.

Elements of the Current Invention

Embodiments of the invention include several combinations of the following: five data structures, two types of packages, and four types of notification and response messages.

Whole Slide Image

The first data structure is a Whole Slide Image (also known as Whole Slide Image Data, WSI or WSI Data) 122 (FIG. 1). This is produced through the capture of an image of a Biological Specimen 102 (FIG. 1) by a digitizer or other image producing capture device.

Patient Data

The next data structure is Patient Data (also known as Patient Metadata) 132 (FIG. 1), which is the sum of patient data captured in other data stores, including but not limited to the originating node's HIS 105 (FIG. 1, equivalently referred to as Hospital Information System), LIS 104 (FIG. 1, equivalently referred to as Laboratory Information System), EMR 103 (FIG. 1, equivalently referred to as Electronic Medical Record) or other data captured to aid the Study review process.

Image Metadata

The next data structure is Image Metadata, which may include Image Capture Data 142 (FIG. 1), containing metadata about the capture of the WSI (resolution, settings, date, technician), Image Analysis Data 143 (FIG. 1), which may contain information about the image determined through User Specific Image Processing, such as cell counts, measurements or statistics, and Metadata from Image Library 144 (FIG. 1), which may contain references to other studies with similar attributes (as determined through language based search of symptoms or diagnosis information, or through image analysis and image search), or any additional, relevant diagnostic information.

User Specific Image Data

The next data structure is User Specific Image Data 120 (FIG. 1). User Specific Image Data 120 is data which is generated in the Packaging Process (FIG. 3) from the WSI Data 122. User Specific Image Data 120 may include, but is not limited to, Automated Image Analysis Data 211 (FIG. 2), Feature and Object Detection Data 212 (FIG. 2), Predictive Coding Data 213 (FIG. 2), Compressed Sensing Data 214 (FIG. 2), Image Tiling Data (FIG. 2-215) and Progressive Image Streaming Data 216 (FIG. 2).

User Specific Metadata

The next data structure is User Specific Metadata, which takes the form of both User Specific Patient Data 130 (FIG. 1) and User Specific Image Metadata 140 (FIG. 1). User Specific Metadata is data which is a result of collecting Patient Metadata and Other Data. The transformation of this data may include but is not limited to filtered or Restricted Patient Data 221 (FIG. 2), EMR Data and References 222 (FIG. 2), Metadata from an Image Library 232 (FIG. 2) or Image Metadata 230 (FIG. 2). Image metadata 230 may include but is not limited to capture metadata 231 or analysis data 233 produced during Automated Image Analysis including but not limited to measurements, cell counts, chromosome counts or other analysis data.

Package

The next data structure is a Package (also referred to as a Detailed Study or Study) 110 (see FIG. 1), which consists of one or more progressively-rich resolution images combined with additional metadata. A preferred embodiment provides access to a plurality of image tiles or a stream of image tiles providing on-demand access to regions (x, y, and z locations and magnification) of the images as they are viewed by the consuming node. A second preferred embodiment pushes or pulls the entire image from the originating node to the consuming node, caching the image for future consumption. The metadata may also be realized in a progressive manner, by providing on-demand access to additional patient metadata that is related to but not contained within the study 110 itself (such as but not limited to additional patient history, results of previous pathology studies, non-pathological study results, detailed studies other than the current study). Data which is added to a package 110 may undergo various User Specific Processing 330 (FIG. 3) to reduce, transform, compress or enhance the WSI Data 122 (FIG. 1), Patient Data 132 (FIG. 1), Image Capture Data 142 (FIG. 1), Image Analysis Data 143 (FIG. 1) and Metadata From Image Library 144 (FIG. 1) which has been included in the package 110 to produce a package which is most appropriate for a Target User 325 (FIG. 3).

Preview Study

The next data structure is the Preview Study, which contains one or more samples of the study images which provide a survey of the study images, combined with both image metadata 140, 230 and patient metadata 130, 220. The preview study itself forms its own package which has undergone a separate Packaging Process (FIG. 3) to reduce the image metadata and patient metadata to provide sufficient data to make a decision on further routing of the review request 150, or enable a decision on whether to fulfill (accept) a review request 150, without including all of the available (and relevant to a full diagnosis) information. A preview study is a form of Recursive Diagnostic Request (FIG. 8) based on Sector Specific Packaging (FIG. 7), where the goal is not a pathologic review, but is instead a decision on whether to perform a review, which would trigger a separate package generation and Pathology Analysis request 150.

Pathology Analysis Request

The next data structure is the Pathology Analysis Request 150 (FIG. 1). This message provides the details and routing necessary for a Target User 325 to be notified that a Package 110 is ready for his review. It may contain a Preview Study and/or a reference to a Detailed Study. Additionally, the Pathology Analysis Request 150 contains addressing and routing information, and any policies and constraints on the study, such as (but not limited to) priority, expiration, expiration after acceptance, reimbursement rates, and number of authorized reviews. This data structure may include various metadata about the desired Pathology Diagnosis, including but not limited to Review Criteria 152 (specific diagnosis instructions, preliminary diagnosis or diagnosis templates) and Routing, Assignment and Scheduling Information 153 (cardinality, expiration, priority). FIG. 1 is illustrative.

Pathology Analysis

The final data structure is the Pathology Analysis (also referred to as a Review, Pathology Review, Pathology Diagnosis or Diagnosis) 160, 550 (FIGS. 1 and 5) which is returned by the consuming node to the originating node if the package 110 contains a Request for Pathology Analysis 150. The Pathology Analysis 160, 550 may contain a Pathology Review 162 (FIG. 1) which contains a detailed written or audio diagnosis and Annotations and Notes 163 (FIG. 1), which may include a series of annotations (x, y, and z locations, zoom factors and notations) or images, as well as review metadata. The review metadata may contain, but is not limited to, physician metadata, review date and time, duration of review, and detail of what elements of the Study were consumed.

Notification, Notification Acceptance and Completion Notification

The message data structures 240 of the invention includes Notification 241, Notification Acceptance 242 and Completion Notification 243.

As illustrated in FIG. 3, a message 355 of Notification Message 241 (FIG. 2) type is sent to a consuming node by an originating node. It may include a Pathology Analysis Request 150 (FIG. 1), as well as any details about the available package 110.

When the Target User 325 accepts or rejects the package 110 for review, a Notification Acceptance Message 242 (FIG. 2) may be returned to the originating node such as at 356 in FIG. 3. The acceptance message 242, 356 signals either the acceptance or rejection of the review request 150 by the consuming node. In the event of an acceptance message 242, 356, if the review request 150 included a plurality of consuming nodes, if the review request's cardinality (number of requested reviews) has been met, a "broadcast acceptance" message is sent to all remaining consuming nodes. This broadcast message signals that the review request has been conditionally fulfilled and that no additional acceptance messages 242, 356 will be processed for the review request 150. In a preferred embodiment, the Preview Study remains cached on the consuming node for the duration of the contention lock of the review request acceptance. If the lock expires, the Review Request 150 is once again forwarded to the remaining recipients for processing.

When the Target User 325 completes a Pathology Analysis 160, 550 (FIGS. 1 and 5), a Completion Notification Message 243, 365 (FIGS. 2 and 3) is returned to the Originating Node from the Consuming Node including the Pathology Analysis 160, 550.

The Packaging Process

The Packaging Process (FIG. 3) is the creation of a Study by an Originating Node for one or more Target Users 325 (FIG. 3). The first step of the packaging process is the acquisition 310 (FIG. 3) of one or more Whole Slide Images 122 (FIG. 1) of one or more Biological Specimens 102 (FIG. 1) which have been taken from a Patient 101 (FIG. 1), prepared and digitized. Once acquired, those WSI(s) 122 are added to a Package 110 (FIG. 1). Next, at least one target user 325 is identified (in the Determine User process 320 of FIG. 3).

Once the user(s) is identified, User Specific Processing 330 may occur (FIG. 3). The user specific processing initially includes User Specific Image Processing (FIG. 6), but may also include retrieving 420 patient data (FIG. 4) and performing User Specific Processing on Patient Data 430 (FIG. 4).

The package 110 may be targeted to a user who has specific business needs or is a member of a specific sector which may dictate the inclusion or exclusion of some image or metadata, and which may dictate whether a Pathology Analysis Request 150, 520 will be added to the package 110. One embodiment of this Sector Specific Processing (also known as Business Requirement Enhanced User Specific Processing—FIG. 7) is for a Primary (720) or Secondary Pathology Analysis (by a Tumor Board, or a second opinion or consult—740) of the package, or for Education or Research (730). For Education, additional data about multiple patients or linking multiple slides from various Patients may be included (at 731, FIG. 7), and for research, criteria and specifics of the clinical study may be included (at 731, FIG. 7).

A preferred embodiment of this Sector Specific Processing (FIG. 7) is to prepare a preview package which may be used for the purposes of notifying multiple users that Request for Diagnosis (Notification 355) and corresponding Package 110 are ready, and that those users should assess the preview package to determine whether they would like to perform the desired analysis. In this way, packages 110 with data which has been filtered to protect patient data may be easily distributed to multiple users or organizations, in order to receive a more rapid, high-quality diagnosis, as the first qualified user with available resources may accept the package 110 and perform the pathology review.

User Specific and Specialized Image Processing

User Specific Image Processing (FIG. 6) may include Automated Image Analysis 660 (FIG. 6), Feature and Object Detection 670 (FIG. 6), both of which are performed on an User Specific Image Data 680 (FIG. 6) which has had Specialized Image Processing performed on it. The Specialized Image Processing (FIG. 6) may include but is not limited to the segmentation and tiling of the WSI Data, the Application of Predictive Coding 620, the application of Compressed Sensing 630, Image Tiling 640 and the preparation of the Progressive Image Data 650 for the Target User 325.

Progressive Image Streaming and Session Sampling

Once the data is prepared, the Image may be progressively streamed (FIG. 9) to the Target User 325, 910 in response to requests for specific regions and resolutions. Only the necessary components of the Progressive Image Data required to recover the requested portions of the image will be included in the Progressive Image Stream 990.

As the Progressive Image Stream 990 is assembled and sent to the Target User 325, 910, Session Sampling Data is recorded at the Originating Node (FIG. 10). Session Sampling Data 1040 (FIG. 10) includes the absolute or relative times, regions and resolutions which were assembled into the Progressive Image Stream 990 to the Target User 325, 910 in response to their request.

Session Sampling Data Transformation, Auditing and Collaboration

The Session Sampling Data 1040 captured during Progressive Image Streaming (FIG. 9) has multiple uses. In one non-Temporal embodiment, it may be used as a security and audit tool, enabling the monitoring and tracking of where, when and by whom an image was accessed, in conjunction with what was accessed. In a second non-Temporal embodiment, a visual representation of what was accessed and at what resolutions may be generated to aid in education of Pathologists or in assisting additional physicians in the review of a particular case or package 110. In a Temporal embodiment, the Session Sampling Data 1040 may be used as a session replay tool to replay the session after the fact, or to mirror the session in real-time to a plurality of users as part of a shared session.

In one embodiment of a non-temporal session, the detailed account of what is accessed from the Session Sampling Data 1040, 1140 can be reduced into a pixel and resolution representation of what was accessed, in conjunction with the start and end times of the session access. FIG. 11 at step 1151 is illustrative.

In a preferred non-Temporal embodiment, there is a non-Temporal Image 1152 (FIG. 11). In the non-Temporal Image 1152 each region and resolution is represented in image fashion in a two dimensional pyramid representation of the image. The color of the viewed resolution is the color of the mapped image, where a higher-resolution sample takes precedence over a lower-resolution sample.

A preferred temporal embodiment is a real-time based list of progressive image data 1154 (FIG. 11), which, in conjunction with the original Progressive Image Data 1160 (FIG. 11) can reconstruct the Progressive Image Stream 1180 (FIG. 11). This stream can be used for later audit of a Progressive Image Stream Session.

Another preferred temporal embodiment is similar to above, but allows for a mirrored session between multiple Target Users (FIG. 12) by sampling the Session Sampling Data 1040, 1140 in real-time. As Target User 1 is requesting a portion of the image through a Progressive Request, the request is fulfilled 1210 (FIG. 12) and Session Sampling Data is generated 1220 (FIG. 12). Target User 2, who has entered into the same session, is Requesting a Mirrored Image Stream at step 1230 (FIG. 12), which incorporates Transforming the Session Sampling Data 1231 (FIG. 12) to produce a Progressive Image Stream 1180, 1240 (FIGS. 11 and 12) for Target User 2. In a further, preferred embodiment, all users in the system have control of the stream, and may generate progressive requests based upon navigation of the image, resulting in additional Progressive Image Streams 1280 and Mirrored Image Streams. Steps 1250, 1260, 1270, 1280 in FIG. 12 are illustrative.

Utilizing the Session Sampling Data 1040, 1140 in another way, a preferred embodiment enables a Target User 910, 1330 to cache a copy of the viewed Progressive Image Stream 990, 1180, 1240, 1280 on his local or associated Consuming Node 1320 system (FIG. 13). In this embodiment, the Originating Node 1310 (FIG. 13), in response to a Request for Image Data 1340 from the Target User 1330 on the Consuming Node 1320, transmits a Progressive Image Stream 1370 representing a portion of the User Specific Image 1350. On the Consuming Node 1320, the Progressive Image Stream is cached 1380 (FIG. 13) as it is forwarded to the Target User 1330. In a further embodiment, when the Target User 1330 terminates its viewing session the Originating Node 1310 generates an secondary Progressive Image Stream 1390 (FIG. 13) which comprises the necessary components needed to transform the Cached Image Data 1380 into a full duplicate version of the original User Specific Image 335, 930, 1350 (FIGS. 3, 9 and 13).

While this invention has been particularly shown and described with references to example embodiments thereof, it will be understood by those skilled in the art that various changes in form and details may be made therein without departing from the scope of the invention encompassed by the appended claims.

What is claimed is:

1. A computer-based method of distributing biological sample data, comprising: acquiring a digital image of a subject biological sample;
   processing the acquired digital image and image capture data according to at least one user, resulting in processed image data and capture metadata, the processed image data representing biological sample data of the subject biological sample;
   through a package processing, combining the processed image data and capture metadata into a Package; and
   enabling simultaneous electronic access to the Package by multiple users, across multiple sectors, in addition to the one user,
   wherein the package processing additionally includes the user requested patient data and user requested metadata in the Package, wherein the step of processing includes patient data processing and user processing, each comprising:
   patient data processing including retrieval, inclusion of data from external data stores, resulting in the user requested patient data; and
   user processing including retrieval and inclusion of image metadata and secondary data from external data stores, as well as further processing secondary data into the user requested metadata.

2. A computer-based method of distributing biological sample data, comprising: acquiring a digital image of a subject biological sample;
   processing the acquired digital image and image capture data according to at least one user, resulting in processed image data and capture metadata, the processed image data representing biological sample data of the subject biological sample;
   through a package processing, combining the processed image data and capture metadata into a Package; and
   enabling simultaneous electronic access to the Package by multiple users, across multiple sectors, in addition to the one user,
   wherein the package processing additionally includes the user requested patient data and user requested metadata in the Package, wherein the one user is a pathologist, and the step of enabling electronic access includes enabling the user to perform a diagnostic processing step, wherein the user records data regarding the biological sample data, the recorded data comprising a written or audio diagnosis, subsampled image data, annotations and comments.

3. The method as claimed in claim 2, wherein the diagnostic processing step is performed partially or wholly by an automated system.

4. A computer-based method of distributing biological sample data, comprising: acquiring a digital image of a subject biological sample;
   processing the acquired digital image and image capture data according to at least one user, resulting in processed image data and capture metadata, the processed image data representing biological sample data of the subject biological sample;
   through a package processing, combining the processed image data and capture metadata into a Package; and
   enabling simultaneous electronic access to the Package by multiple users, across multiple sectors, in addition to the one user,
   wherein the package processing additionally includes the user requested patient data and user requested metadata in the Package, wherein the step of processing includes a modeling process including any one or combination of transmission, storage and classification modeling methods,
   wherein transmission modeling includes combinations of channel coding and version controlled conditional transmission,
   storage modeling includes at least source coding, and
   classification modeling includes combinations of predictive encoding, compressed sensing, and progressive image streaming.

5. The method as claimed in claim 1, wherein the step of processing is aggregate processing, comprising the aggregation of user specifications for two or more users, and, wherein the step of enabling electronic access resolves the package data for each user according to his respective user-specification, as if each individual User Request were independently processed.

6. The method as claimed in claim 1, wherein one or more of the user processing, patient data processing or package processing steps initiates a complete or partial diagnostic processing step as an input to its own processing step.

7. A computer-based method of distributing biological sample data, comprising: acquiring a digital image of a subject biological sample;
processing the acquired digital image to form a progressive image stream representing biological sample data of the subject biological sample; and
processing additionally including preparation of access to the progressive image stream, said access being in terms of resolution, scale and sub-regions of the biological sample;
transmitting the progressive image stream to one or more users, such that a user views spatially progressive images, in terms of resolution, scale and sub-regions, of the subject biological sample, and
recording a list of processed image data requested by a user, said list being recorded as session sampling data,
wherein the session sampling data is able to be recalled in a manner enabling auditing of portions of an image viewed by the user,
wherein the processing additionally includes the user requested patient data and user requested metadata in the Package, wherein the step of acquiring acquires a series of images, and the step of processing employs compressed sensing.

8. The method as claimed in claim 7, wherein the session sampling data is able to be recalled and accessed as unordered data providing an overview of image portions that the user accessed.

9. The method as claimed in claim 7, wherein the session sampling data is recalled and accessed in an order in which the user accessed and reviewed the processed image data, allowing reconstruction of a session.

10. The method as claimed in claim 7, wherein a plurality of session sampling data for a same image may be sampled to gather information about common points across multiple sessions.

11. The method as claimed in claim 7, wherein the session sampling data is recalled by one or more other users as it is being generated, resulting in all users having a synchronized viewing experience.

12. The method as claimed in claim 10, further comprising enabling a user involved in the synchronized viewing experience to (a) navigate the processed image data, resulting in additional progressive image stream requests, and (b) annotate the image viewed, said annotating being in a manner viewable by the other users.

13. The method as claimed in claim 7, wherein the user accesses the requested processed image data remotely and the session sampling data is augmented by a locally cached copy of the requested processed image data.

14. The method as claimed in claim 12, further comprising enabling the cached copy of the processed image data to be further processed to include the entirety of the image data.

15. The method as claimed in claim 7, further comprising processing the image by at least one of: applying predictive coding, applying a compressed sensing, employing image tiling, and employing progressive streaming.

16. The method as claimed in claim 1, further comprising processing the image by at least one of: applying predictive coding, applying a compressed sensing, employing image tiling, and employing progressive streaming.

17. The method as claimed in claim 2, further comprising processing the image by at least one of: applying predictive coding, applying a compressed sensing, employing image tiling, and employing progressive streaming.

18. The method as claimed in claim 4, further comprising processing the image by at least one of: applying predictive coding, applying a compressed sensing, employing image tiling, and employing progressive streaming.

* * * * *